United States Patent [19]

Sherry et al.

[11] Patent Number: 5,362,476
[45] Date of Patent: Nov. 8, 1994

[54] ALKYL PHOSPHONATE POLYAZAMACROCYCLIC CHEATES FOR MRI

[75] Inventors: A. Dean Sherry, Dallas, Tex.; Garry E. Kiefer, Lake Jackson, Tex.

[73] Assignees: Board of Regents, The University of Texas System, Austin, Tex.; Dow Chemical Company, Midland, Mich.

[21] Appl. No.: 923,715

[22] Filed: Jul. 31, 1992

Related U.S. Application Data

[63] Continuation-in-part of Ser. No. 615,619, Nov. 19, 1990, abandoned, which is a continuation-in-part of Ser. No. 357,193, May 25, 1989, abandoned, and Ser. No. 291,053, Dec. 28, 1988, Pat. No. 4,983,376, which is a continuation-in-part of Ser. No. 7,729, Jan. 27, 1987, abandoned, which is a continuation-in-part of Ser. No. 662,075, Oct. 18, 1984, Pat. No. 4,639,365.

[51] Int. Cl.$^5$ .................. A61B 5/055; A61B 31/675; C07D 225/00; C07D 255/02
[52] U.S. Cl. ........................ 424/9; 540/465; 540/474; 514/79; 514/836; 436/173; 128/653.4; 534/15
[58] Field of Search ............. 424/9; 540/465, 474; 514/79, 836; 436/173, 806; 128/653.4, 654; 534/15

[56] References Cited

U.S. PATENT DOCUMENTS

| | | | |
|---|---|---|---|
| 3,930,867 | 1/1976 | Bigelow | 260/256.4 |
| 3,932,451 | 1/1976 | Bigelow | 260/309.6 |
| 3,987,128 | 10/1976 | Richman | 260/936 |
| 3,996,276 | 12/1976 | Atkins | 260/561 P |

(List continued on next page.)

FOREIGN PATENT DOCUMENTS

| | | |
|---|---|---|
| 0232751A1 | 8/1987 | European Pat. Off. ... C07D 273/00 |
| 0287465A1 | 10/1988 | European Pat. Off. ... C07D 257/02 |
| 0292689A2 | 11/1988 | European Pat. Off. ... C07D 257/02 |
| 0374929A1 | 6/1990 | European Pat. Off. ... C07D 257/02 |
| 382582 | 8/1990 | European Pat. Off. . |
| 0404605 | 12/1990 | European Pat. Off. . |
| 0448191A1 | 9/1991 | European Pat. Off. ... C07D 257/02 |
| 0485045A2 | 5/1992 | European Pat. Off. ... C07D 257/02 |
| 2539996 | 1/1984 | France . |
| 3129906 | 7/1981 | Germany . |
| 3401052 | 1/1989 | Germany . |
| 1529150 | 9/1977 | United Kingdom . |
| 2137612 | 1/1984 | United Kingdom . |
| 1081169 | 3/1984 | U.S.S.R. . |
| WO92/08725 | 5/1992 | WIPO ..................... C07F 9/6515 |

OTHER PUBLICATIONS

Kabachnik, M. I., et al., "Synthesis and Study of a New Complexone—N,N',N"-Tris-(Dihydroxyphosphoryl-methyl)-1,4,7-Triazacyclononane", *Izv. Akad. Nauk. SSSR, Ser. Khim.*, pp. 769–777 (1984) English translation, published in the Soviet Union.

(List continued on next page.)

*Primary Examiner*—Gary E. Hollinden
*Attorney, Agent, or Firm*—Arnold, White & Durkee

[57] ABSTRACT

The present invention relates to a new polyazamacrocyclic compound or a salt thereof and its uses as a tissue specific chelator. The compound has the formula

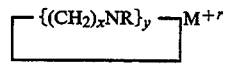

where
x is 2, 3 or a combination of p 2(s) and q 3(s) where p+q=y;
y is 4;
R is ($CH_2)_zP(=O)OR^1OR^2$;
$R^1$ is H or $CH_3$;
$R^2$ is $C_nH_{1+2n}$;
n is 4 to 6;
z is 1 to 3.
M is a heavy metal ion.

These compounds may be used for magnetic resonance imaging.

6 Claims, 2 Drawing Sheets

U.S. PATENT DOCUMENTS

| | | | |
|---|---|---|---|
| 4,038,312 | 7/1977 | Atkins | 260/551 P |
| 4,085,106 | 4/1978 | Atkins | 260/551 P |
| 4,130,715 | 12/1978 | Atkins | 260/551 P |
| 4,337,154 | 6/1982 | Fukuchi | 210/490 |
| 4,352,751 | 10/1982 | Wieder | 260/112 R |
| 4,421,671 | 12/1983 | Cusano | 252/301.4 |
| 4,432,907 | 2/1984 | Wieder | 260/420 |
| 4,472,509 | 9/1984 | Gansow | 436/548 |
| 4,639,365 | 1/1987 | Sherry | 424/9 |
| 4,647,447 | 3/1987 | Gries et al. | 424/9 |
| 4,731,239 | 3/1988 | Gordon | 424/9 |
| 4,735,796 | 4/1988 | Gordon | 424/9 |
| 4,775,522 | 11/1988 | Clark, Jr. | 424/9 |
| 4,889,931 | 12/1989 | Rocklage et al. | 540/465 |
| 4,957,939 | 9/1990 | Gries et al. | 424/9 |
| 4,963,344 | 10/1990 | Gries et al. | 424/9 |
| 4,983,376 | 1/1991 | Sherry | 424/9 |
| 5,236,695 | 8/1993 | Winchell et al. | 424/9 |

OTHER PUBLICATIONS

Grubbs, Robert D. and Maguire, Michael E., "Magnesium as a Regulatory Cation: Criteria and evaluation", *Magnesium* 6:113–127 (1987) published in Europe.

Fry, C. H., "Measurement and Control of Intracellular Magnesium Ion Concentration in Guinea Pig and Ferret Venticular Myocardium", *Magnesium* 5:306–316 (1986) published in Europe.

Cabbiness et al., "Macrocyclic Effect on the Stability of Copper(II) Tetramine Complexes", *J. Am. Chem. Soc.*, 91(23):6540 (1969), published in USA.

Martin et al., "The Relationship between Metal-Donor Distance and Ring Size in Macrocyclic Complexes", *J. Am. Chem. Soc.*, 96(12):4046 (1974), published in USA.

Richman et al., "Nitrogen Analogs of Crown Ethers", *J. Am. Chem. Soc.*, 96(7):2268–70 (1974), published in USA.

Lettvin et al., "Communications: Gd(TTHA): An Aqueous Carbon-13 Relaxation Reagent," *J. Mag. Res.*, 28:459–61 (1977), published in Europe.

White et al., "A Tris(dialkylamino)phosphine with Pyramidal Nitrogens," *J. Amer. Chem. Soc.*, 101(17):4921 (1979), published in USA.

Desreux, "Nuclear Magnetic Resonance Spectroscopy of Lanthanide Complexes with a Tetraacetic Tetraaza Macrocycle. Unusual Conformation Properties," *Inorganic Chemistry*, 19:1319–24 (1980), published in USA.

Sherry, "A Proposal on Basic Chemical Research," submitted to the Robert A. Welch Foundation (1981), printed in USA.

Bryden et al., "Multinuclear NMR Study of Three Aqueous Lanthanide Shift Reagents: Complexes with EDTA and Two Macrocyclic Ligands," *Chemical Abstracts*, No. 97:206960z (1982), published in USA.

Brasch et al., "Contrast-Enhanced NMR Imaging: Animal Studies Using Gadolinium–DTPA Complex," *American Journal of Roentgenology*, 142:625–30 (1984), published in USA.

Chen et al., "Paramagnetic Metalloporphyrins as Potential Contrast Agents in NMR Imaging," *Fed. Euro. Biochem. Soc.*, 168(1):70 (1984), published in Europe.

Goldstein et al., "Gadolinium DTPA (An NMR Proton Imaging Contrast Agent): Chemical Structure, Paramagnetic Properties and Pharmacokinetics," *Physiol. Chem. & Phys. & Med. NMR*, 16:97–104 (1984), published in USA.

Weinmann et al., "Characteristics of Gadolinium–DTPA Complex: A Potential NMR Contrast Agent," *American Journal of Roentgenology*, 142:619–24 (1984), printed in USA.

Wolf, "Contrast Enhancement in Biomedical NMR," *Physiol. Chem. & Phys. & Med. NMR*, 16:93–95 (1984), printed in USA.

Geraldes et al., "Nuclear Magnetic Resonance and Potentiometric Studies of the Protonation Scheme of a Triaza Triacetic Macrocycle and Its Complexes with Lanthanum and Lutetium," *Inorganic Chemistry*, 24(23):3876 (1985), printed in USA.

Geraldes et al., "Lanthanum-139 Nuclear Magnetic Resonance Studies of Polyaminocarboxylate-Lanthanum Complexes in Aqueous Solution," *Journal of Magnetic Resonance*, 66:274–82 (1986), published in USA.

Geraldes et al., "Magnetic Field Dependence of Solvent Proton Relaxation Rates Induced by $Gd^{3+}$ and $Mn^{2+}$ Complexes of Various Polyaza Macrocyclic Ligands: Implications for NMR Imaging," *Magnetic Resonance in Medicine*, 3:242–50 (1986), published in USA.

Sherry et al., "Nuclear Magnetic Resonance Structural Studies of an Axially Symmetric Lanthanide Ion Chelate in Aqueous Solution," *Journal of Magnetic Resonance*, 66:511–24 (1986), published in USA.

(List continued on next page.)

OTHER PUBLICATIONS

Carafoli & Penniston, "The Calcium Signal," *Sci. Amer.*, 253:70–78, 1985, published in USA.

Charton et al. "Spontaneous and Evoked Release of Endogenous $Zn^{2+}$ in the Hippocampal Mossy Fiber Zone of the Rat in Situ," *Ex. Brain Res.*, 58:202–206, 1985, published in Europe.

Veloso et al., "The Concentrations of Free and Bound Magnesium in Rat Tissues," *J. Biol. Chem.*, 248(13):4811–4819, 1973, published in USA.

Lopez et al., "Direct Measurement of Intracellular Free Magnesium in Frog Skeletal Muscle Using Magnesium-Selective Microelectrodes," *Biochim. Biophys. Acta*, 804:1–7, 1984; published in Europe.

Brinley & Scarpa, "Ionized Magnesium Concentration in Axoplasm of Dialyzed Squid Axons," *FEBS Letters*, 50(1):82–85, 1975, published in Europe.

Rink et al., "Cytoplasmic pH and Free $Mg^{2+}$ in Lymphocytes," *J. Cell. Biol.*, 95:189–196, 1982, published in USA.

Corkey et al., "Regulation of Free and Bound Magnesium in Rat Hepatocytes and Isolated Mitochondria," *J. Biol. Chem.*, 261:2567–2574, 1986, published in USA.

Smith et al., "Intracellular Calcium Measurements by $^{19}F$ NMR of Fluorine-Labeled Chelators," *Proc. Natl. Acad. Sci. USA*, 80:7178–7182, 1983, published in USA.

Metcalfe et al., "Free Cytosolic $Ca^{2+}$ Measurements with Fluorine Labelled Indicators Using $^{19}FNMR$," *Cell Calcium*, 6:183–195, 1985, published in Europe.

Levy et al., "Measurement of Cytosolic Free Magnesium Ion Concentration by $^{19}F$ NMR," *Biochemistry*, 27:4041–4048, 1988, published in USA.

Murphy et al., "Cytosolic Free Magnesium Levels in Ischemic Rat Heart," *J. Biol. Chem.*, 264(10):5622–5627, 1989, published in USA.

Marban et al., "Intracellular Free Calcium Concentration Measured with $^{19}F$ NMR Spectroscopy in Intact Ferret Hearts," *Proc. Natl. Acad. Sci. USA*, 84:6005–6009, 1987, published in USA.

Irving et al., "A Study of Some Problems in Determining the Stoicheiometric Proton Dissociation Constants of Complexes by Potentiometric Tetrations Using a Glass Electrode," *Analytic Chimica Acta*, 38:475–488, 1967, published in Europe.

Caceci & Cacheris, "Fitting Curves to Data," *Byte*, 5:340–362, 1984, published in USA.

Geraldes et al., "Synthesis, Protonation Sequence, and NMR Studies of Polyazamacrocyclic Methylenephosphonates," *Inorg. Chem.*, 28:3336–3341, 1989, published in USA.

Cortes et al., "Potentiometry and NMR Studies of 1,5,9-Triazacyclododecane-N,N',N"-Triacetic Acid and Its Metal Ion Complexes," *Inorg. Chem.*, 29:5–9, 1990, published in USA.

Gupta et al., "The Determination of the Free Magnesium Level in the Human Red Blood Cell by $^{31}P$ NMR," *J. Biol. Chem.*, 253(17):6172–6176, 1978, published in USA.

Flatman & Lew, "Use of Ionophore A23187 to Measure and To Control Free and Bound Cytoplasmic Mg in Intact Red Cells," *Nature*, 267:360–362, 1977, published in Europe.

Bevilacqua et al., "Equilibrium and Thermodynamic Study of the Aqueous Complexation of 1,4,7-Triazacyclononane-N,N',N"-Triacetic Acid with Protons, Alkaline-Earth-Metal Cations, and Copper(II)," *Inorg. Chem.*, 26:2699–2706, 1987, published in USA.

Broan et al., "Synthesis of New Macrocyclic Amino-Phosphinic Acid Complexing Agents and their C-and P-Functionalised Derivatives for Protein Linkage," *Synthesis*, pp. 63–68, Jan./Feb., 1992, published in Europe.

Broan et al., "Synthesis and Complex Stability of Parent and C-Functionalised Derivatives of 1,4,7-Triazacyclononane-1,4,7-tris[methylene(methylphosphinic acid)]: An Effective New Complexing Agent," *J. Chem. Soc., Chem. Commun.*, pp. 1738–1739, published in Europe.

Lazar and Sherry, "N,N',N"-Tris(methoxymethyl)-1,4,7-triazacyclononane: a New Synthetic Tool for the Synthesis of Tris-N-substituted 1,4,7-Triazacyclononane Derivatives," *J. Chem. Soc. Chem.* 1252–1253, 1991.

ALKYL PHOSPHONATE POLYAZAMACROCYCLIC CHEATES FOR MRI

This is a continuation-in-part of U.S. Ser. No. 07/615,619 filed Nov. 19, 1990, which is a continuation-in-part of U.S. Ser. No. 07/357,193 filed May 25, 1989 and now abandoned. and U.S. Ser. No. 07/291,053 filed Dec. 28, 1988, the latter now issued as U.S. Pat. No. 4,983,376. All of the above applications are incorporated by reference herein. Application Ser. No. 07/291,053 was a continuation-in-part of application Ser. No. 007,729 filed on Jan. 27, 1987, and now abandoned, which was a continuation-in-part of application Ser. No. 662,075, filed on Oct. 18, 1984, now issued as U.S. Pat. No. 4,639,365.

BACKGROUND OF THE INVENTION

FIELD OF THE INVENTION

The present invention relates to compositions and methods for enhancing contrast in imaging internal structures and functions of living subjects.

IMAGING MODALITIES

Imaging of internal structures and functions of living subjects may be accomplished by applying electromagnetic radiation from external sources (as in conventional x-rays and computerized axial tomography) or internal sources (as in PET or positron emission tomography and radionuclide scans). Use of ionizing radiation is avoided in imaging with nuclear magnetic resonance (NMR) and untrasonography, making these methods advantageous for many applications.

Whatever the imaging modality, consideration is given to means of increasing image contrast through localization of contrast agents in the region to be imaged. Such agents are frequently metals which emit, absorb, or scatter energy or, as in the case with NMR agents, increase the image signal strength locally. For best effect, agents must be localized. This may be accomplished, for example, by direct injection of contrast agent (as in myelograms or retrograde urethrograms), through metabolic uptake of an agent (as in PET), and by conjugation of contrast agents with monoclonal antibodies which tend to accumulate in certain tissues. The latter process in particular has been used in NMR image enhancement with chelated metal ions. Though well known, the process has several shortcomings:

1—preparation of the antibody is complex;
2—diminished immunoreactivity of the antibody occurs following conjugation;
3—there is limited uptake of the conjugate by the target tissue; and
4—there may be unfavorable interactions between the chelated ion and the antibody.

Because of the advantages of NMR imaging (good resolution and avoidance of ionizing radiation), an NMR contrast agent capable of greater localization would be clinically important. Such an agent would offer significant advantages over contrast agents of the prior art.

NMR CONTRAST AGENTS

The quality of the images obtained from an NMR scan is based on two properties: the proton densities of the various tissues and differences in proton relaxation rates. The proton density of tissues cannot be readily altered. Proton relaxation rates can be adjusted by adding a paramagnetic relaxation agent, more commonly known as a "contrast agent." Contrast agents enhance the contrast in NMR images between magnetically similar but histologically dissimilar tissues.

Gadolinium, which has strong paramagnetic properties because of its seven unpaired electrons, has been tested as a contrast agent. It has a large magnetic moment which efficiently relaxes magnetic nuclei and increases tissue contrast in the region of the gadolinium.

One drawback of gadolinium as a contrast agent is its toxicity to animals, although a possible remedy for this problem is incorporation of gadolinium in a compound that would pass through the body and be excreted without releasing toxic gadolinium ions. Unfortunately, the rare earth elements (including gadolinium) do not form stable covalent bonds with organic molecules, so such molecules can decompose in vivo and release the toxic ions.

Thus, there is a need for effective contrast agents which avoid the toxicity problems inherent in using gadolinium or another metal ion. Further, it is desirable that a contrast agent control or influence the distribution of chelated ions in the body.

A even more desirable approach to the site-specific delivery of metal ions would be through use of stable chelates having inherent affinity for various tissue types. Inherent tissue affinity built into the organic chelating agent through modifications in both ionic charge and degree of lipophilic character would offer substantial advantages over currently available agents.

SUMMARY OF THE INVENTION

The present invention relates to a series of new phosphorous-containing triaza- and tetraazamacrocyclic chelators which have inherent affinity for certain tissues. Following intravascular injection, chelates comprising these compositions preferentially accumulate in certain tissues, depending on the time after injection. In particular, 1,4,7,10-tetraazacyclododecane-1,4,7,10-tetra(methylenephosphonate monobutyl ester) has a high affinity for liver tissue and the gastrointestinal tract (in that order). Chelates comprising this agent are thus suitable for liver imaging because of the lipophilic character imparted by the ester functionality. Such agents are not metabolized, and eventually pass out of the body via the urine or feces.

While the monobutyl ester above appears well adapted for liver imaging, analogous alkyl esters have also been considered. Monopentyl esters are nearly as good for liver imaging, but monooctyl esters have the disadvantage of very low aqueous solubility. Monopropyl esters, on the other hand, may be used for liver imaging but are less efficient because a substantial portion of the agent is rapidly lost to the kidneys; monoisopropyl esters would behave similarly. Hence, the most preferred embodiment is that described above with monobutyl esters.

For use with NMR, compositions of the present invention must be chelated with a metallic element. While the element is preferably of the rare-earth series (preferably gadolinium), those skilled in the art will recognize that other metallic ions might also be useful for imaging. For example, other metal chelates (e.g., chelates of radionuclides or heavy metals) may be used for imaging by scintigraphy, x-radiation, and analogous imaging methods where changes in local tissue parameters can increase image contrast. Depending on the metal ion preferred for a particular contrast agent application, either triaza- or tetraaza- compounds of the present invention may be selected as chelators.

Chelators of the present invention have the formula where
x is 2, 3 or a combination of p 2(s) and q 3(s) where p+q=y;
y is 3 or 4;
R is ( $CH_2)_zP(=O)OR^1OR^2$;
$R^1$ is H or $CH_3$;
$R^2$ is butyl, pentyl or hexyl; and
z is 1 to 3.

In one important embodiment, this compound may be complexed with a metal to be a polyazamacrocyclic compound-metal complex having the formula where
x is 2, 3 or a combination of p 2(s) and q 3(s) where p+q=y;
y is 3 or 4;
R is $(CH_2)_zP(=O)OR^1OR^2$;
$R^1$ is H or $CH_3$;
$R^2$ is butyl, pentyl or hexyl;
z is 1 to 3;
r is 2 or 3; and
M is a metal ion.

The y designation characterizes the compound as triazamacrocyclic or tetraazamacrocyclic. The x is preferably 2, although 3 is feasible under many circumstances. Combinations of p 2(s) and q 3(s) for x are of course readily produced but the total of p+q must be y for the number of units in the polyaza macrocycle. H or $CH_3$ for $R^1$ are believed equivalent in use.

In a preferred embodiment of either the compound or its metal complex y is 3, p is 1 and q is 2 or p is 2 and q is 1.

In another preferred embodiment of the compound or its metal complex, y is 4, p is 1 and q is 3, p is 2 and q is 2 or p is 3 and q is 1 and z is most preferably 1. n is preferably 2.

In a more preferred embodiment x is 2, y is 4, z is 1, $R^1$ is H and $R^2$ is butyl.

In another preferred embodiment X is 2, y is 3, z is 1, $R^1$ is H and $R^2$ is butyl.

The $M^{+r}$ is preferably a paramagnetic lanthanide, although other divalent or trivalent metal ions, including radionuclides and heavy metals, may also be so complexed.

In one important application, the present invention involves a method for enhancing a magnetic resonance image of a subject. This method comprises administering to the subject a polyazamacrocyclic compound-metal complex having the formula where x is 2, 3 or a combination of p 2(s) and q 3(s) where p+q=y;
y is 3 or 4;
R is ( $CH_2)_zP(=O)OR^1R^2$;
$R^1$ is H or $CH_3$;
$R^2$ is butyl, pentyl or hexyl;
z is 1 to 3;
r is 3; and
M is gadolinium.

DETAILED DESCRIPTION OF PREFERRED EMBODIMENTS

EXAMPLE 1

Triazamacrocyclic Compounds

NOTPME Synthesis

Materials 1,4,7-triazacyclononane, paraformaldehyde, diethylphosphite, and activated carbon Darco G-60 were purchased from Aldrich Chemical Company. $MgSO_4$ was from Mallickrodt, sodium hydroxide, and benzene from J. T. Baker, and diethylether from Fisher Scientific. All chemicals were of highest purity and were used without further purification. Solutions of $ZnCl_2$, $GdCl_2$, $MgCl_2$ and Ca $Cl_2$ were standardized complexometrically.

Figure 1:
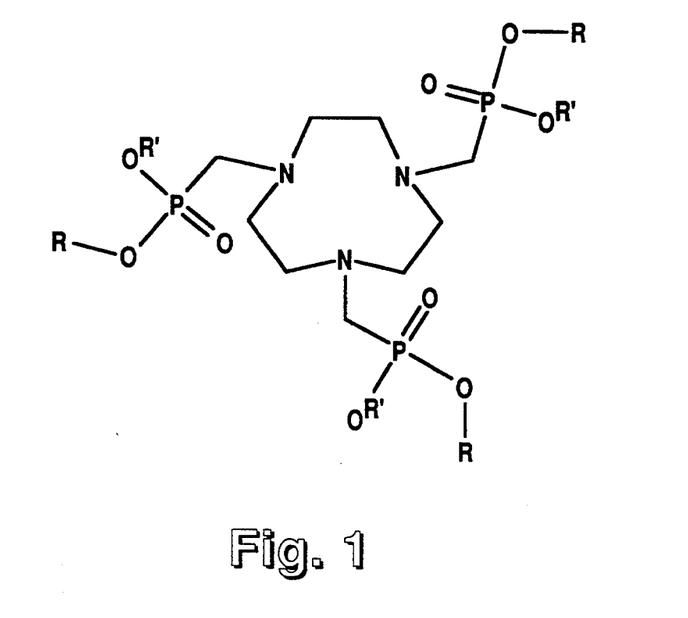
FIG. 1 schematically illustrates the structure of NOTPME (where R is $CH_2CH_3$ and $R^1$ is H).

Synthesis of NOTPME 1,4,7-Triazacyclononane (1.91 g, 14.71 mmol) and diethylphosphite (7.018 g, 16.94 mmol, 15% excess) were dissolved in 125 ml of benzene and heated to reflux. Anhydrous paraformaldehyde (1.727 g, 30% excess) was added in small portions to the above refluxing mixture while the benzene-water azeotropic mixture was removed by distillation. After the addition of paraformaldehyde was complete, the entire solution was boiled for 30 minutes and then evaporated to obtain a yellow viscous oil. The oil was dissolved in 150 ml anhydrous diethylether and dried with anhydrous $MgSO_4$ overnight. $MgSO_4$, along with a white precipitate which formed, were filtered off and discarded. The filtrate was decolorized with activated carbon and filtered. The filtrate was evaporated in vacuum to obtain a viscous oil of 1,4,7-triazacyclononane-N,N',N''-tris(-methylenephosphonate diethylester) (NOTPDE). Pure NOTPDE was obtained in 96% yield (9.21 g, 14.17 mmol) and was used for the synthesis of NOTPME (structure shown in FIG. 1) without further purification.

$^1$H NMR data of NOTPDE in $CDC_3$ (TMS at zero) are as follows: δ (ppm): 1.33 (t, 18H, —$CH_3$), 2.97 (s, 12H, N—$CH_2$), 3.00 (d, 6H, P—$CH_2$), 4.13 (p, 12H, O—$CH_2$).

9.20 g of NOTPDE (14.15 mmol) was mixed with 2.50 g of NaOH in 9 ml H20) and after 2 hours the entire reaction mixture was boiled until a clear solution was obtained (approximately 5 minutes). The solution was cooled to room temperature and was allowed to stand overnight. The crystals formed were filtered off from the viscous mother liquor using a pressure filter funnel with a coarse porosity grade filter disc. The crystals were washed once with cold absolute ethanol, three times with absolute ethanol-diethylether (1:1) mixture and finally with diethyl ether. The crystals of Na$_3$-NOTPME were dried in dry nitrogen stream at 25° C. for 2 hours. Traces of H$_2$O and ethanol were removed upon vacuum drying (10 mm Hg) NOTPME for 5 hours at 50° C. Pure NOTPME thus obtained were white crystals, very hygroscopic, readily soluble in H$_2$O, and fairly soluble in chloroform. The yield of pure NOTPME was 40.8% (3.24 g, 5.77 mmol).

$^1$H NMR (D$_2$O, HDO peak set as reference at 4.90 ppm), δ(ppm): 1.23 (t, 9H, —CH$_3$), 2.54 (s, broad, 6H, P—CH$_2$), 2.79 (s, broad, 12 H, N—CH$_2$), 3.91 (p, 6H, 0—CH$_2$).

EXAMPLE 2

Tetraazamacrocyclic Compounds

DOTEP Synthesis

Figure 2:
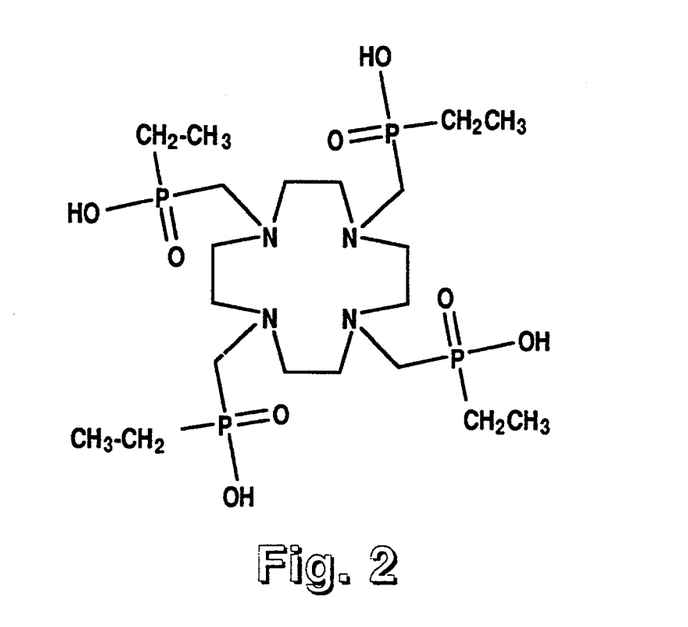
FIG. 2 schematically illustrates the structure of DOTEP.

DOTEP, shown in FIG. 2, was prepared as follows. 2 ml of dichloroethylphosphine was slowly mixed with ice to form the corresponding ethylphosphinic acid. After warming to room temperature, 390 mg of 1,4,7,10-tetraazacyclododecane tetrahydrochloride (cyclen.4HCl) (Parrish Chem. Co., Ogden, Utah) was added and the mixture heated to boiling under a nitrogen atmosphere. A solution containing 157 mg of paraformaldehyde dissolved in 10 ml of 6M HCl was added at a rate of 0.5 ml/hr, while the mixture continued to reflux. The final mixture was refluxed an additional 4 hours then cooled to room temperature. This solution was concentrated under vacuum to a viscous oil, redissolved into 6 ml of water and loaded onto a DOWEX 50Wx4 (hydrogen form) cation exchange column (7.5 ml bed volume). The column was washed to neutrality with water and the product eluted with 60 ml of 0.66M HCl. The fractions containing DOTEP were combined, evaporated, redissolved in absolute ethanol and evaporated to a white solid. This solid was dispersed into anhydrous ether, filtered off, pre-dried under nitrogen and dried under vacuum at 60°-70° C. to yield a white, very hygroscopic solid (360 mg, 44% yield). This solid was stored in sealed ampoules. Elemental analysis and potentiometry shows the solid to be DOTEP.2HCl

EXAMPLE 3

Tetraazamacrocyclic Compounds

DOTP Dibutyl Ester Synthesis

Tetraaza-12-crown-4.4HCl (1 g, 3.14×10$^{-3}$ mol) was dissolved in water and the pH adjusted to 9.0 using 1M NaOH. The solvent was evaporated and the residue dried under vacuum for 1 hour. Formaldehyde (6.6 mL of 37% solution, 7.15 g, 0.24 mol) was added and the solution stirred for 30 minutes at room temperature. Dibutyl phosphite (5.10 mL of 96% purity, 0.025 mol) was then added and the reaction mixture stirred for 15 hours at room temperature (dipentyl and dihexyl phosphite are so used to produce dipentyl and dihexyl esters respectively). The resulting mixture consisted of two layers. The bottom layer was mostly excess formaldehyde, as indicated by $_{13}$C NMR. The upper layer contained the product and excess phosphite. This layer was separated, concentrated and dried under vacuum for 1 hour. The resulting syrup was loaded onto a silica-gel column (2.5×11 cm). The excess phosphite was washed away with methylene chloride (250 mL). The product was eluted with 5% methanol in methylene chloride. 20 mL fractions were collected and monitored by TLC. The fractions containing the product were combined, concentrated, and dried under vacuum,. A pale yellow oil was obtained in 75% yield (2.34 g) . $^1$H NMR (CDCl$_3$): 0.87 (t, J=7.3, 6H), 1.33 (m, J=7.3, 4H), 1.60 (p, J=7.3, 4H), 3.18 (br s, 4H), 3.39 (d, J=8.5, 2H), 4.03 (m, J=7.3, 6.1, 4H). $^{13}$C NMR (CDCl$_3$): 11.3 (s), 16.5 (s), 30.3 (d, J=5.9), 47.3 (d, J=148), 50.0 (br s), 63.8 (d, J=7.3).

EXAMPLE 4

Tetraazamacrocyclic Compounds

DOTP Monobutyl Ester (DOTPMB) Synthesis

The dibutyl ester was suspended in 1M KOH (20 mL). The mixture was stirred at 85° C. for 17 hours and then at 106° C. for 9 hours. The solvent was evaporated and the sample dried under vacuum for 1 hour. Methylene chloride (40 mL) was then added and the remaining solid KOH crushed as much as possible. The solvent was again evaporated and this procedure repeated another two times. The solvent was evaporated and the residue dissolved in methanol (60 mL). The mixture was filtered and then concentrated to a syrup under vacuum. Methylene chloride (80 mL) was added and the mixture filtered. The solvent was evaporated and the residue dried under vacuum to yield a white solid in 71% yield. $^{13}$C NMR (D$_2$O; ref. dioxane at 67.0 ppm): 13.5, 18.9, 32.9 (d, J=5.9), 50.7 (d, J=140.6), 51.5 (br s), 64.6 (d, J=5.9).

EXAMPLE 5

Biodistribution of Gd-DOTPMB

Complexation and Biodistribution

Figure 3:
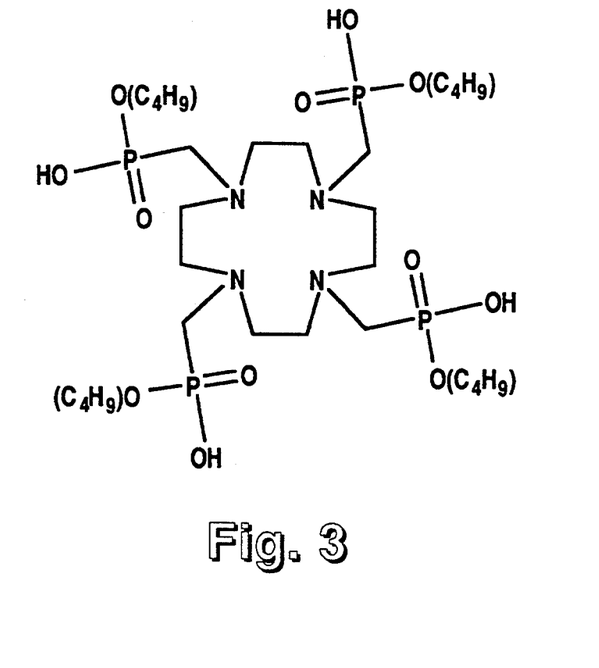
FIG. 3 schematically illustrates the structure of DOTPMB.

A complex of DOTPMB (FIG. 3) and Gd (0.012M based on metal, 2:1 ligand/metal ratio) was prepared and spiked with tracer quantities of Gd-159. Complexation was determined to be greater than 99% by standard analytical methods described in earlier reports. Two Sprague-Dawley rats were then injected with the complex at a 0.05 mmol/kg level. The animals were sacrificed after 30 minutes and dissected for biodistribution data (Tables I and II); actual counts obtained from various tissues are shown in Table II. At the end of this time period, an average of 58% of the injected dose was found in small intestine (see entry for SM INTES in Table I). A similar experiment performed with a third rat yielded 52% in small intestine (Tables III and IV); actual counts obtained from various tissues are shown in Table IV. The bulk of the remaining activity in each case was eliminated via the renal system (Tables II and IV).

In order for localization to occur in the small intestine, the complex must first pass through the liver. Thus, since liver activity at the 30 minute time point (1%) was minimal (see e.g., Table I), the peak of liver localization passed within the prior 30 minutes. This is evident in an example of biodistribution 15 minutes after administration of chelated tracer, which is documented in Tables VIII and IX. Although by 15 minutes the peak of liver localization had passed for mouse 1, with 4% in the liver and 88% in the small intestine, mouse 2 still had a significant liver concentration (66%) at the 15 minute point. These animal models suggest that imaging within 15 minutes after administration of chelated tracer will be necessary for best definition of the liver. The following test description supports that conclusion. Higher doses would, of course, lengthen the time of liver localization at concentrations sufficient to substantially enhance liver imaging.

Gamma Imaging of DOTPMB

A Sm(153)-DOTPMB complex was prepared as described above for gamma imaging of a Sprague-Dawley rat. Images were acquired at one minute intervals over a 16-minute period. The image sequence revealed concentration of the chelate in liver within one minute following injection. The complex is then rapidly transported from the liver to the stomach and small intestine. Tables V, VI and VII contain data taken at 1 hour, 24 hours and 72 hours after injection, showing movement of the agent from stomach and intestine to feces.

TABLE I

| TIME: 30 Minute Biodistribution | | | |
|---|---|---|---|
| DATE | LIGAND | METAL | COMMENTS |
| 8/6/91 | DOTPMB-K, | Gd-159, | 99% Complexation |
| 4:1, LIG:MET Molar Ratio, (Metal = 3 × 10 − 4 M) | | | |

TABLE I-continued

| TIME: 30 Minute Biodistribution | | | |
|---|---|---|---|
| DATE | LIGAND | METAL | COMMENTS |
| 8/6/91 | DOTPMB-K, | Gd-159, | 99% Complexation |
| 4:1, LIG:MET Molar Ratio, (Metal = 3 × 10 − 4 M) | | | |
| BONE | 0.281 | 0.106 | 0.193 | 0.124 |
| TAIL | 0.212 | 0.191 | 0.201 | 0.015 |
| LIVER | 1.234 | 0.755 | 0.994 | 0.339 |
| KIDNEY | 0.392 | 0.299 | 0.346 | 0.066 |
| SPLEEN | 0.009 | 0.011 | 0.010 | 0.002 |
| MUSCLE | 0.658 | 0.506 | 0.582 | 0.108 |
| BLOOD | 0.299 | 0.250 | 0.274 | 0.035 |
| HEART | 0.011 | 0.000 | 0.006 | 0.008 |
| LUNG | 0.158 | 0.029 | 0.094 | 0.091 |
| BRAIN | 0.004 | 0.004 | 0.004 | 0.001 |
| STOMACH | 0.574 | 0.530 | 0.552 | 0.031 |
| SM INTES | 80.304 | 36.405 | 58.354 | 31.041 |
| LG INTES | 0.591 | 0.433 | 0.512 | 0.112 |

TABLE II (see legend for Table I)

| DATA | COUNTS | ORGAN | N ENTER WT | BCKG COR | % DOSE/G | % DOSE |
|---|---|---|---|---|---|---|
| 1 | | Std A | X Rat 1 Wt | 0 | | |
| | 10510 | Std B | X 216.72 | 0 | | |
| 2 | 414838 | Std C | av 414404.5 | 414405 | | |
| 3 | 480 | Bone | 0.60 | 47 | 1.87E − 02 | 2.81E − 01 |
| 4 | 1311 | Tail | 2.74 | 878 | 7.73E − 02 | 2.12E − 01 |
| 5 | 5546 | Liver | 10.86 | 5113 | 1.14E − 01 | 1.23E + 00 |
| 6 | 2058 | Kidney | 2.32 | 1625 | 1.69E − 01 | 3.92E − 01 |
| 7 | 469 | Spleen | 0.75 | 36 | 1.14E − 02 | 8.57E − 03 |
| 8 | 478 | Muscle | 1.52 | 45 | 7.06E − 03 | 6.58E − 01 |
| 9 | 576 | Blood | 1.62 | 143 | 2.12E − 02 | 2.99E − 01 |
| 10 | 481 | Heart | 0.82 | 48 | 1.40E − 02 | 1.15E − 02 |
| 11 | 1088 | Lung | 1.25 | 655 | 1.26E − 01 | 1.58E − 01 |
| 12 | 449 | Brain | 1.62 | 16 | 2.31E − 03 | 3.74E − 03 |
| 13 | 2811 | Stomach | | 2378 | | 5.74E − 01 |
| 14 | 333215 | Sm Intes | | 332782 | | 8.03E + 01 |
| 15 | 2883 | Lg Intes | | 2450 | | 5.91E − 01 |
| 16 | 150310 | Urine | | 149877 | | 3.62E + 01 |
| 17 | 400 | Urine | | 0 | | 0.00E + 00 |
| 18 | 428 | Urine | | 0 | | 0.00E + 00 |
| 19 | 443 | BKG | 228.17 | | WT Rat 2 | |
| 20 | 451 | Bone | 0.67 | 18 | 6.30E − 03 | 1.06E − 01 |
| 21 | 1225 | Tail | 2.82 | 792 | 6.77E − 02 | 1.91E − 01 |
| 22 | 3561 | Liver | 10.96 | 3128 | 6.89E − 02 | 7.55E − 01 |
| 23 | 1674 | Kidney | 2.38 | 1241 | 1.26E − 01 | 2.99E − 01 |
| 24 | 480 | Spleen | 0.53 | 47 | 2.12E0 − 02 | 1.12E − 02 |
| 25 | 469 | Muscle | 1.66 | 36 | 5.16E − 03 | 5.06E − 01 |
| 26 | 559 | Blood | 1.80 | 126 | 1.68E − 02 | 2.50E − 01 |
| 27 | 430 | Heart | 0.85 | 0 | 0.00E + 00 | 0.00E + 00 |
| 28 | 554 | Lung | 1.28 | 121 | 2.27E − 02 | 2.91E − 02 |
| 29 | 452 | Brain | 1.55 | 19 | 2.88E − 03 | 4.46E − 03 |
| 30 | 2629 | Stomach | | 2196 | | 5.30E − 01 |
| | 151297 | Sm Intes | | 150864 | | 3.64E + 01 |
| | 2229 | Lg Intes | | 1796 | | 4.33E − 01 |
| | 116731 | Urine | | 116298 | | 2.81E + 01 |
| | 901 | Urine | | 468 | | 1.13E − 01 |
| | 423 | Urine | | 0 | | 0.00E + 00 |
| | 424 | BKG | | 0 | | |

BKG AVG = 434

4:1, LIG:MET Molar Ratio, (Metal = 3 × 10 − 4 M)

| | % DOSE/GRAM | | | |
|---|---|---|---|---|
| | RAT 1 | RAT 2 | AVERAGE | ± |
| WEIGHT | 216.72 | 228.17 | 222.45 | 8.096 |
| BONE | 0.019 | 0.006 | 0.01 | 0.009 |
| TAIL | 0.077 | 0.068 | 0.07 | 0.007 |
| LIVER | 0.114 | 0.069 | 0.09 | 0.032 |
| KIDNEY | 0.169 | 0.126 | 0.15 | 0.031 |
| SPLEEN | 0.011 | 0.021 | 0.02 | 0.007 |
| MUSCLE | 0.007 | 0.005 | 0.01 | 0.001 |
| BLOOD | 0.021 | 0.017 | 0.02 | 0.003 |
| HEART | 0.014 | 0.000 | 0.01 | 0.010 |
| LUNG | 0.126 | 0.023 | 0.07 | 0.073 |
| BRAIN | 0.002 | 0.003 | 0.00 | 0.000 |

0.000 = NO ACTIVITY DETECTED

DOSE

TABLE III

| TIME: 30 Minute Biodistribution | | | |
|---|---|---|---|
| DATE | LIGAND | METAL | COMMENTS |
| 8/6/91 | DOTPMB-K, | Gd-159, | 99% Complexation |
| 4:1, LIG:MET Molar Ratio, (Metal = 3 × 10 − 4 M) | | | |

| | % DOSE/GRAM |
|---|---|
| | RAT 3 |
| WEIGHT: 235.14 | |
| Bone | 0.006 |
| Tail | 0.013 |
| Liver | 0.016 |
| Kidney | 0.121 |
| Spleen | 0.000 |
| Muscle | 0.000 |
| Blood | 0.000 |
| Heart | 0.000 |

TABLE III-continued

TIME: 30 Minute Biodistribution

| DATE | LIGAND | METAL | COMMENTS |
|---|---|---|---|
| 8/6/91 | DOTPMB-K, | Gd-159, | 99% Complexation |

4:1, LIG:MET Molar Ratio, (Metal = $3 \times 10^{-4}$ M)

| | % DOSE/GRAM RAT 3 |
|---|---|
| Lung | 0.009 |
| Brain | 0.004 |

0.000 = No Activity Detected

| | |
|---|---|
| Bone | 0.109 |
| Tail | 0.038 |
| Liver | 0.196 |
| Kidney | 0.303 |
| Spleen | 0.000 |
| Muscle | 0.026 |
| Blood | 0.000 |
| Heart | 0.000 |
| Lung | 0.012 |
| Brain | 0.005 |
| Stomach | 0.012 |
| Sm Intes | 51.549 |
| Lg Intes | 2.232 |

TABLE IV (see legend for Table III)

| DATA | COUNTS | ORGAN | N ENTER WT | BCKG COR | % DOSE/G | % DOSE |
|---|---|---|---|---|---|---|
| 1 | | Std A | X Rat 1 Wt | 0 | | |
| 1 | | Std B | X 235.14 | 0 | | |
| 2 | 414367 | Std C | av 413946 | 413946 | | |
| 3 | 439 | Bone | 0.69 | 18 | 6.30E − 03 | 1.09E.01 |
| 4 | 578 | Tail | 2.95 | 157 | 1.29E − 02 | 3.79E − 02 |
| 5 | 1232 | Liver | 11.96 | 811 | 1.64E − 02 | 1.96E − 01 |
| 6 | 1675 | Kidney | 2.51 | 1254 | 1.21E − 01 | 3.03E − 01 |
| 7 | 418 | Spleen | 0.66 | 0 | 0.00E + 00 | 0.00E + 00 |
| 8 | 423 | Muscle | 1.91 | 2 | 2.53E − 04 | 2.56E − 02 |
| 9 | 412 | Blood | 1.84 | 0 | 0.00E + 00 | 0.00E + 00 |
| 10 | 417 | Heart | 0.85 | 0 | 0.00E + 00 | 0.00E + 00 |
| 11 | 470 | Lung | 1.25 | 49 | 9.47E − 03 | 1.18E − 02 |
| 12 | 442 | Brain | 1.28 | 21 | 3.96E − 03 | 5.07E − 03 |
| 13 | 470 | Stomach | | 49 | | 1.18E − 02 |
| 14 | 213806 | Sm Intes | | 213385 | | 5.15E + 01 |
| 15 | 9661 | Lg Intes | | 9240 | | 2.23E + 00 |
| 16 | 102818 | Urine | | 102397 | | 2.47E + 01 |
| 17 | 12520 | Urine | | 12099 | | 2.92E + 00 |
| 18 | 447 | Urine | | 26 | | 6.28E − 03 |
| 19 | 1421 | BKG | | | | |

BKG AVG = 421

TABLE V

One Hour Biodistribution, Imaged Rat
TIME: One Hour biodistribution

| DATE | LIGAND | METAL | COMMENTS |
|---|---|---|---|
| 8/8/91 | DOTPMB-K, D. | Sm = 153 | 99% Complex |

4:1, LIG:MET Molar Ratio (Metal = $3 \times 10^{-4}$ M)

| | % DOSE/GRAM | % DOSE |
|---|---|---|
| WEIGHT: 263.82 | | |
| Bone | 0.004 | 0.067 |
| Tail | 0.038 | 0.093 |
| Liver | 0.014 | 0.144 |
| Kidney | 0.084 | 0.245 |
| Spleen | 0.016 | 0.011 |
| Muscle | 0.001 | 0.078 |
| Blood | 0.001 | 0.019 |
| Stomach | | 45.144 |
| Sml Int | | 31.408 |
| Lrg Int | | 0.003 |

TABLE VI

Hour Biodistribution, Imaged Rat
TIME: 24 Hour biodistribution

| DATE | LIGAND | METAL | COMMENTS |
|---|---|---|---|
| 8/8/91 | DOTPMB-K | Sm = 153 | 99% Complex |

4:1, LIG:MET Molar Ratio (Metal = $3 \times 10^{-4}$ M)

| | % DOSE/GRAM | % DOSE |
|---|---|---|
| WEIGHT: 263.82 | | |
| Bone | 0.008 | 0.146 |
| Tail | 0.015 | 0.036 |
| Liver | 0.010 | 0.106 |
| Kidney | 0.154 | 0.451 |
| Spleen | 0.029 | 0.020 |
| Muscle | 0.017 | 1.883 |
| Blood | 0.000 | 0.004 |
| Stomach | | 0.053 |
| Smll Int | | 2.109 |
| Smll Int | | 19.611 |
| Lrg Int | | 8.351 |
| Feces | | 35.981 |
| Urine | | 2.799 |
| Paper | | 0.126 |

TABLE VI

Rat Injected: 8/8/91
TIME: 24 hour biodistribution

| Date | Ligand | Metal | Comments |
|---|---|---|---|
| 8/12/91 | DOTPMB-K | Sm = 153 | 99% Complex |

4:1, LIG:MET MOLAR RATIO (Metal = $3 \times 10^{-4}$ M)

| | % DOSE/GRAM | % DOSE |
|---|---|---|
| WEIGHT: 269.58 | | |
| Bone | 0.014 | 0.219 |
| Tail | 0.002 | 0.005 |
| Liver | 0.002 | 0.030 |
| Kidney | 0.019 | 0.054 |
| Spleen | 0.000 | 0.000 |
| Muscle | 0.000 | 0.000 |
| Blood | 0.000 | 0.000 |
| Feces | | 5.832 |
| Feces | | 5.467 |
| Feces | | 2.464 |
| Urine | | 0.077 |
| Bladder | | 0.242 |

TABLE VIII

File = BTY15STD Summary Standardized Data Mouse #2
(15 minute biodistribution), 99% complex, 25.0 UL dose
Ca added to complex at 1;1 molar, lig: Ca

| DATE | LIGAND | METAL | COMMENTS |
|---|---|---|---|
| 10/30/91 | DOTPME-K | Sm-153 | #08-07-91 |

2:1, Lig:Met Molar Ratio, (Metal = $3 \times 10 - 4$ M), pH 7 — = 8

| | % DOSE/GRAM | | |
|---|---|---|---|
| | MOUSE 1 | MOUSE 2 | AVERAGE |
| WEIGHT | 15.854 | 10.702 | 13.278 |
| BONE | 0.171 | 3.169 | 1.670 |
| TAIL | 1.374 | 83.296 | 42.335 |
| LIVER | 3.979 | 66.441 | 35.210 |
| KIDNEY | 0.889 | 14.568 | 7.728 |
| SPLEEN | 1.260 | 0.831 | 1.046 |
| MUSCLE | 0.173 | 1.437 | 0.805 |
| BLOOD | 43.105 | 3.743 | 23.424 |
| HEART | 0.472 | 2.418 | 1.445 |
| LUNG | 0.697 | 2.735 | 1.716 |
| BRAIN | 0.023 | 0.139 | 0.081 |
| TUMOR | 0.648 | 4.844 | 2.746 |
| STOMACH | 14.272 | 4.343 | 9.308 |
| SMALL INT. | 88.504 | 40.343 | 64.423 |
| LARGE INT. | 3.320 | 2.298 | 2.809 |
| URINE | 0.000 | 0.000 | 0.000 |
| BODY 1 | 0.408 | 1.637 | 1.022 |
| BODY 2 | 0.148 | 5.594 | 2.871 |

*MOUSE 2 DID NOT BECOME ACTIVE AFTER ANESTHESIA, HOWEVER ALIVE***

TABLE IX

| | % DOSE | |
|---|---|---|
| | MOUSE 1 | MOUSE 2 |
| BONE | 0.149 | 2.100 |
| LIVER | 3.379 | 37.732 |
| KIDNEY | 0.199 | 3.610 |
| SPLEEN | 0.095 | 0.039 |
| MUSCLE | 1.179 | 6.615 |
| BLOOD | 44.420 | 2.604 |
| HEART | 0.033 | 0.157 |
| LUNG | 0.090 | 0.210 |
| BRAIN | 0.010 | 0.054 |
| TUMOR | 0.062 | 0.237 |
| STOMACH | 3.565 | 0.586 |
| SMALL INT. | 86.734 | 27.837 |
| LARGE INT. | 2.994 | 1.145 |
| URINE | 12.857 | 0.007 |
| BODY 1 | 2.294 | 6.890 |
| BODY 2 | 0.585 | 17.147 |

Changes may be made in the construction, operation and arrangement of the various parts, elements, steps and procedures described herein without departing from the concept and scope of the invention as defined in the following claims.

What is claimed is:

1. A method for increasing contrast of nuclear magnetic resonance images of a patient, the method comprising
administering to a patient needing nuclear magnetic resonance imaging a diagnostically effective amount of a polyazamacrocyclic compound or a salt thereof, the compound having the formula where
x is 2, 3 or a combination of p 2(s) and q 3(s) where p+q=y;
y is 4;
R is $(CH_2)_zP(=O)OR^1OR^2$;
$R^1$ is H or $CH_3$;
$R^2$ is $C_nH_{1+2n}$;
n is 4 to 6;
z is 1 to 3;
r is 2 or 3; and
M is a metal ion; and obtaining a magnetic resonance image of the patient.

2. The method of claim 1 wherein x is 2, y is 4, z is 1, and n is 4.

3. The method of claim 1 wherein M is a lanthanide element.

4. The method of claim 1 wherein M is $Gd^{+3}$.

5. A method for increasing contrast of nuclear magnetic resonance images of a patient, the method comprising
administering to a patient needing nuclear magnetic resonance imaging a diagnostically effective amount of a polyazamacrocyclic compound or a salt thereof, the compound having the formula where
x is 2, 3 or a combination of p 2(s) and q 3(s) where p+q=y;
y is 4;
R is $(CH_2)_zP(=O)OR^1OR^2$;
$R^1$ is H;
$R^2$ is $C_4H_9$;
z is 1 to 3;
r is 2 or 3; and
M is a metal ion; and obtaining a magnetic resonance image of the patient.

6. The method of claim 5 where $M^{+r}$ is $Gd^{+3}$.

* * * * *